US00PP25406P3

(12) United States Plant Patent
Lewis

(10) Patent No.: US PP25,406 P3
(45) Date of Patent: Apr. 7, 2015

(54) APPLE TREE NAMED 'LEWIS'

(50) Latin Name: *Malus domestica Borkh*
Varietal Denomination: Lewis

(71) Applicant: Brandon Lewis, East Wenatchee, WA (US)

(72) Inventor: Brandon Lewis, East Wenatchee, WA (US)

( * ) Notice: Subject to any disclaimer, the term of this patent is extended or adjusted under 35 U.S.C. 154(b) by 63 days.

(21) Appl. No.: 13/815,821

(22) Filed: Mar. 15, 2013

(65) Prior Publication Data

US 2014/0283238 P1 Sep. 18, 2014

(51) Int. Cl.
*A01H 5/00* (2006.01)

(52) U.S. Cl.
USPC ..... Plt./161

(58) Field of Classification Search
USPC ..... Plt./161, 172
See application file for complete search history.

*Primary Examiner* — Kent L Bell
(74) *Attorney, Agent, or Firm* — Klarquist Sparkman, LLP

(57) ABSTRACT

A new apple variety obtained from a limb sport of a 'Honeycrisp' apple tree, the new variety being distinguished by a much-improved red color and improved resistance to bitter pit disorder.

4 Drawing Sheets

Latin name of the genus and species of the plant claimed: *Malus domestica* Borkh.

Variety denomination: 'Lewis'.

BACKGROUND OF THE INVENTION

The present invention relates to a new and distinct variety of apple tree named 'Lewis'. The new tree resulted from asexual propagation of plant material from a naturally occurring sport that I discovered in September of 2005 growing on a 'Honeycrisp' apple tree (U.S. Plant Pat. No. 7,197) in an orchard in Rock Island, Wash. I took dormant wood from the limb sport in March of 2006 and grafted this wood onto some existing apple trees of an unknown variety in my orchard in East Wenatchee, Wash. One of these trees still survives. Subsequently, at my direction, 40 trees were budded onto 'Budagovsky 9' (unpatented) understock. This budding took place in September of 2007, with the budding being performed in Quincy, Wash. These trees were subsequently transplanted to my orchard in East Wenatchee, Wash. An additional group of 3,200 trees of my new variety were budded on 'M9-337' (unpatented) rootstock in August of 2011 in my nursery in Quincy, Wash.

The observations of plant characteristics found in this description are from the trees that were budded in 2007, and hence can be considered to be fourth-leaf from planting or five year old trees.

BRIEF SUMMARY OF THE INVENTION

The 'Lewis' cultivar is distinguished from the 'Honeycrisp' apple cultivar because of the following unique combination of characteristics: Apples that consistently have 70%-90% of their surface area that is a solid red blush; and low susceptibility to bitter pit disorder.

FIG. 4 shows a typical apple of my 'Lewis' variety on the left and a typical apple of the 'Honeycrisp' variety on the right. These apples were both picked on the same day from trees growing in East Wenatchee, Wash., and were photographed the next day. The photograph exemplifies the more intense red color of apples of my new variety in comparison to 'Honeycrisp' apples.

Asexual reproduction of this new variety budded onto 'Budagovsky 9' rootstock in Quincy, Wash. and observation of the resulting trees growing in East Wenatchee, Wash. has shown that the foregoing characteristics are firmly fixed and come true to type.

The following detailed description is based upon observations of the five year old trees of my new variety that were asexually propagated by budding in 2007 in Quincy, Wash. and that are now growing in my orchard in East Wenatchee, Wash.

Certain characteristics of this new variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to Munsell Book of Color, Kollmorgen Instruments Corp. 405 Little Britain Road, New Windsor, N.Y. 12553. The colors of photographs may vary with lighting and other conditions and, therefore, color characteristics of this new variety should be determined with reference to the observations described herein, rather than from the photographs alone.

DETAILED DESCRIPTION

Figure 1:
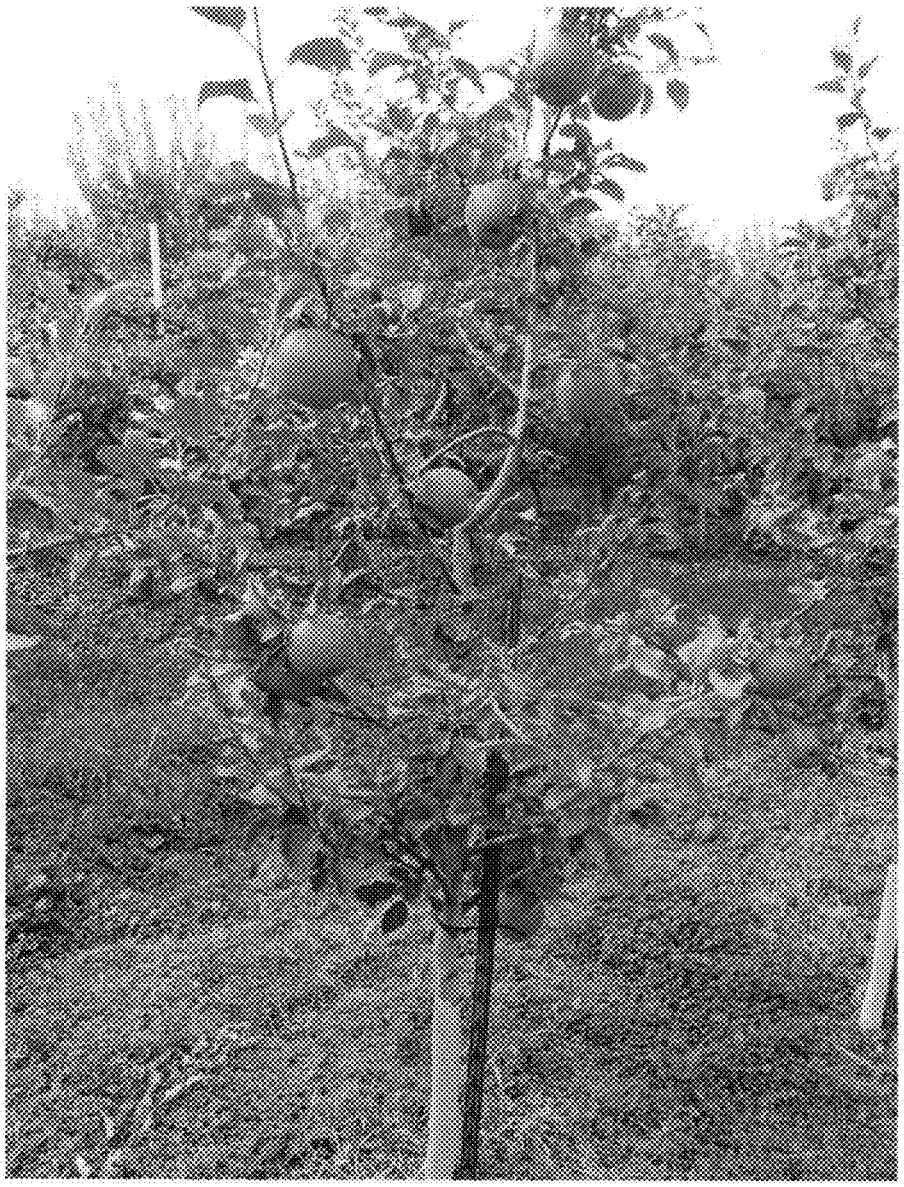
FIG. 1 is a photograph of a representative apple on a tree limb of a tree of the 'Lewis' variety growing in East Wenatchee, Wash., taken in September of 2012.
Figure 2:
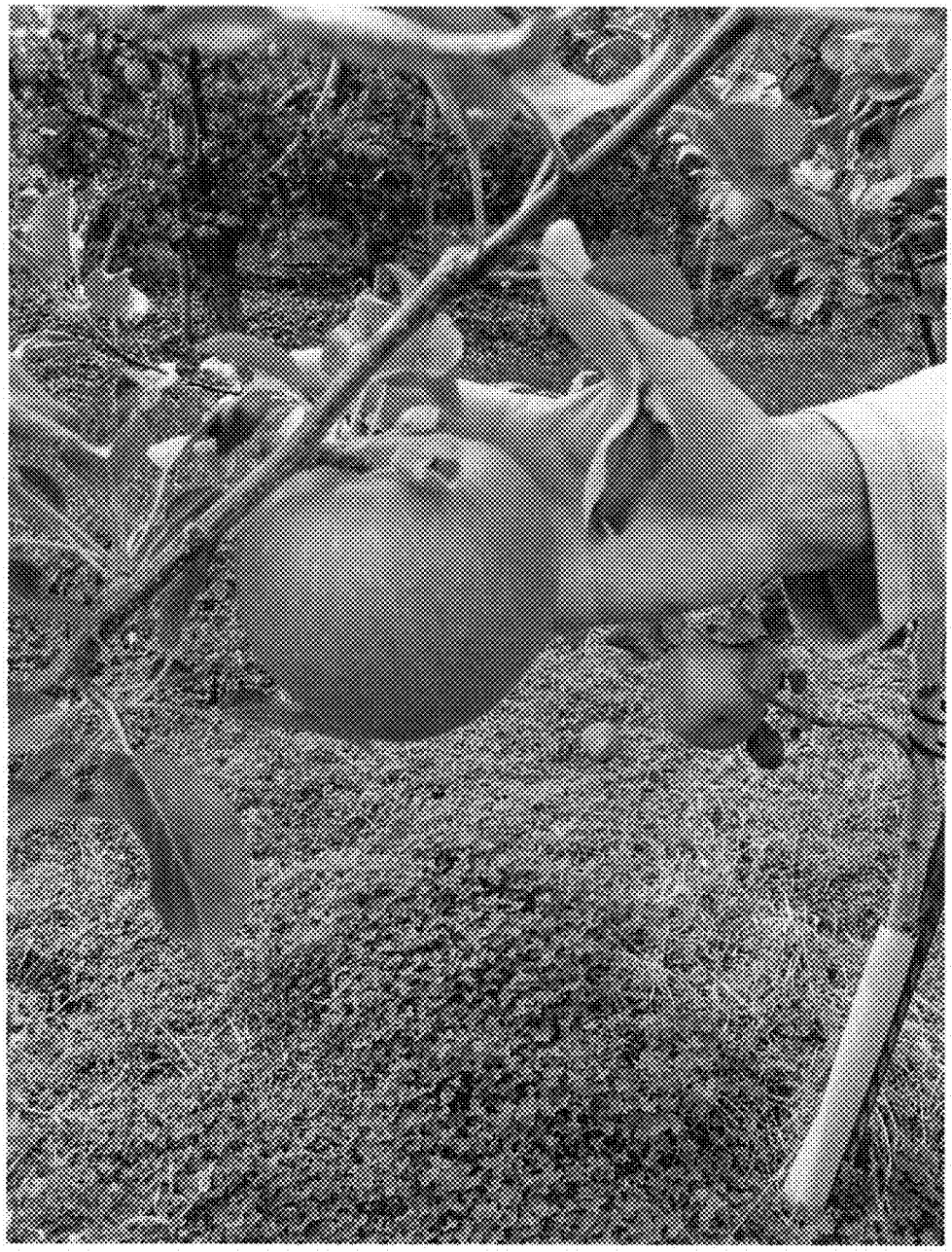
FIG. 2 is a photograph of cross-sections of representative apples of the 'Lewis' variety, taken at the same time as the photograph of FIG. 1.
Figure 3:
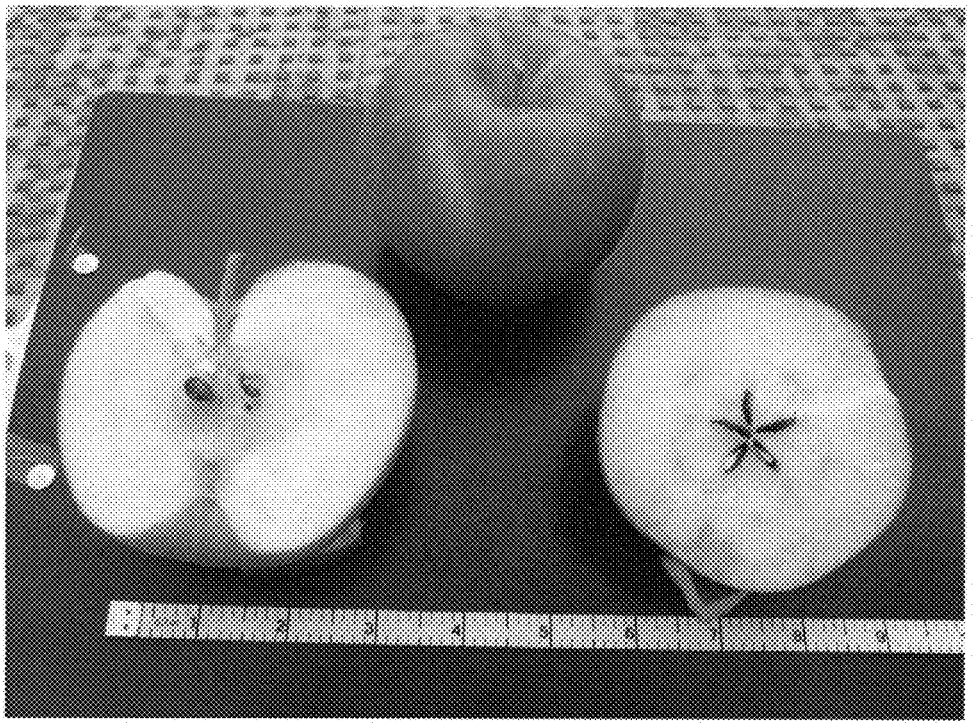
FIG. 3 is a photograph of a five year old fruit bearing 'Lewis' tree, growing in East Wenatchee, Wash.
Figure 4:
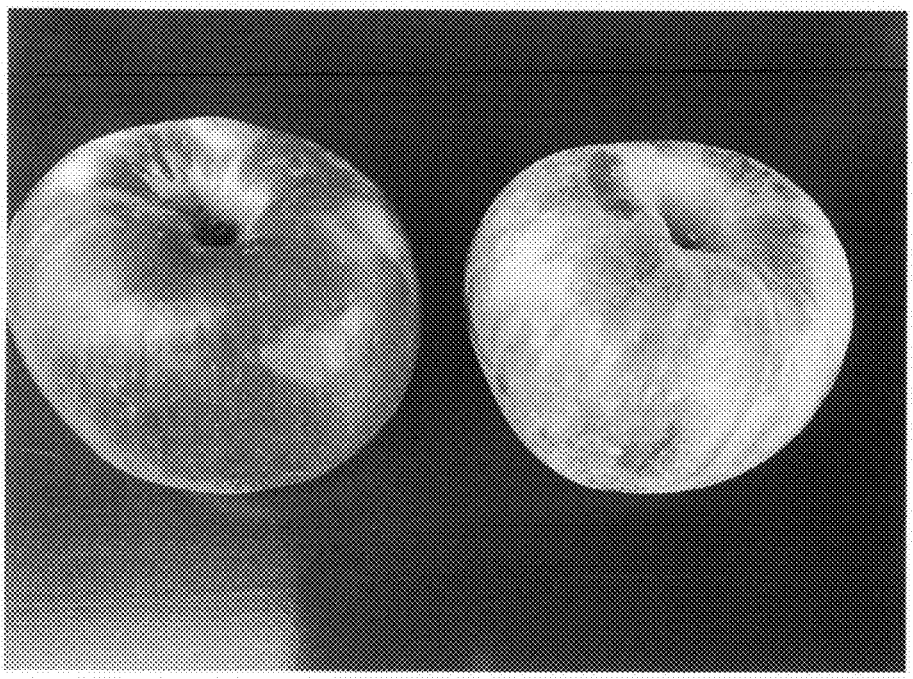
FIG. 4 is a photograph of representative 'Lewis' (on the left) and standard 'Honeycrisp' (on the right) apples harvested on the same day in East Wenatchee, Wash. and photographed the following day.

The following detailed description of the 'Lewis' variety is based on observations of the five year old trees of my new variety. The observed progeny were growing on 'Budagovsky 9' rootstock in my orchard in East Wenatchee, Wash.

Scientific name: *Malus domestica* Borkh.

Varietal name: 'Lewis'.

Parentage: Trees propagated from a limp sport of 'Honeycrisp' (U.S. Pat. No. 7,197).

Tree:

*Vigor*.—Moderate.

*Habit*.—Upright, spreading.

*Height*.—About 6 feet (five year old trees).

*Width*.—About 3 feet (five year old trees).

*Trunk*.—Diameter of five year old trees is 1¼ inches measured at 12 inches above the budding union.

*Trunk bark texture*.—Smooth.

*Trunk bark color*.—Gray Brown (10 YR 6/2).

*Trunk lenticels*.—Color: Tan (10 YR 7/6).

*Trunk lenticel shape*.—Round, oblong.

*Trunk lenticel size*.—1/16" ×3/32".

*Branch length*.—One year old branches 12-16"; diameter ¼" to 3/16".

*Crotch angle of branches*.—60-80°.

*Bearing*.—On spurs.

*Branch color*.—One-year-old branches are Brown (10 YR 3/6).

*Branch pubescence*.—Colorless pubescence over entire length of new branch growth.

*Branch lenticels*.—Density is approximately 30 per square inch on 1-year-old branch, typical branch lenticels are mostly round, occasionally oval, and measure about 1/64" in diameter.

*Branch lenticel color*.—Tan (10 YR 7/6).

*Internode length*.—Typical internode length is about 1¼ inches on one-year-old branches.

*Bearing*.—Bearing has been annual for the 2011 and 2012 growing seasons.

*Winter hardiness*.—Hardy in East Wenatchee Wash., Hardiness Zone 4.

*Disease resistance*.—For the most part, 'Lewis' has disease resistance identical to 'Honeycrisp', moderate scab resistance, susceptible to powdery mildew, unknown resistance to fire blight. However, unlike 'Honeycrisp', the 'Lewis' cultivar demonstrates greater resistance to bitter pit. These trees had no bitter pit manifestation in spite of receiving no calcium spray application. This is in contrast to the weekly sprays necessary to prevent bitter pit from occurring in the standard 'Honeycrisp' trees growing in the same area of East Wenatchee, Wash.

Leaves: Based upon observations of ten typical 'Lewis' tree leaves observed on Jul. 25, 2012.

*Texture*.—Surface smooth.

*Sheen*.—Medium glossy upper surface; lower surface dull.

*Length*.—From about 2½ inches to about 3¼ inches, averaging about 3 inches.

*Width*.—About 1¾ inches to 2½ inches.

*Thickness*.—About 1/128 of an inch.

*Petiole*.—About 1 to 1½ inches long, and about 1/16 of an inch in diameter; color Dark Green (2.5 GY 4/4).

*Margin*.—Finely serrated.

*Overall shape*.—Long oblong.

*Tip shape*.—Acute to acuminate.

*Base shape*.—Obtuse.

*Stipules*.—Mostly lacking, except at branch tip; 2 opposite in arrangement; Light Green (2.5 GY 7/4) in color; shape narrow; length about ⅜ of an inch long; width about 1/32 of an inch.

*Leaf color*.—

*Upper leaf surface*.—Green (2.5 GY 4/4).

*Lower leaf surface*.—Green (2.5 GY 5/4).

*Vein upper surface*.—Medium Green (2.5 GY 5/6).

*Vein lower surface*.—Light Green (2.5 GY 7/6).

*Pubescence*.—Upper surface glabrous.

*Lower surface pubescence*.—(2.5 GY 9/2).

Flowers:

*Buds*.—Quantity: 4 to 6 buds per spur.

*Bud size*.—Three-eighths of an inch long by ¼ of an inch in diameter.

*Flower size when open*.—One-and-a-quarter inches to 1½ inches in diameter.

*Color*.—Tight bud: Deep Rose (7.5 RP 4/10); Petal color: fully open flower: Pale Pink (7.5 RP 9/2) to pure white, with more Pink (7.5 RP 6/8) along veins of petals of the inside surface of the flower. Color of the outside surface of a fully opened flower: Pale Pink (7.5 RP 8/4 to 7.5 RP 9/2) to pure white.

*Pedicel*.—Light Green (5 GY 7/4); size about 1 inch long by 1/16 inch in diameter.

*Petals*.—5 petals per flower; petal size about 1 inch long by ½ inch wide; arrangement: overlapping slightly. Petal shape is wide ovate. Petal apex is rounded. Petal margin: smooth and free. Petal base is rounded. Upper surface (inside) texture is slightly rippled. Lower (outside) petal texture is slightly fluted.

*Sepals*.—Quantity per flower 5; position: typical, recurved downward; overall shape is deltoid; the apex is acuminate; sepal margin is smooth and pubescent, length about ½"; width about 3/16"; color of both upper and lower surfaces: Medium Green (5 GY 6/6).

*Stamens*.—Number: 10-18.

*Anthers*.—Quantity per flower 10-18; renal shaped; width about 1/16 of an inch; length about 3/32 of an inch; pollen color: Bright Yellow (5Y 8/12).

*Filaments*.—Length ¼"; color: Cream (7.5 Y 9/4).

*Pistil*.—Length 5/16".

*Styles*.—Number 5; form: joined at base; average length about ⅜ of an inch; color: Cream (7.5 Y 9/4).

*Ovary*.—Length ⅛ of an inch; color light green (5 GY 7/4); pubescent.

*Stigma*.—Shape: Irregular, oblong, clubbed; color: Medium Brownish Yellow (2.5 Y 6/10).

*Peduncle*.—Length about ⅛ of an inch to about ¼ of an inch; color: Dull Green (5 GY 7/4); finely pubescent; approximately 3/16" in diameter at base. Similar to standard 'Honeycrisp' trees.

*Pollination requirement*.—Presumed to be diploid, self-sterile, like standard 'Honeycrisp' trees.

Bloom season: Initial bloom date in 2012 observed in East Wenatchee, Wash.: Apr. 25, 2012. Full bloom date in 2012 observed in East Wenatchee, Wash.: Apr. 30, 2012.

Fruit: Observations from a limited sampling of typical fruit in a laboratory that were obtained on Sep. 17, 2012, from a 'Lewis' tree growing in East Wenatchee, Wash.

*Size*.—Very large, from about 2¾ to 3½ inches long and 3¼ to 3¾ inches at widest point.

*Position of maximum diameter*.—Just above the equator.

*Form*.—Round conic.

*Ribbing*.—Absent.

*Stem cavity*.—1¼ to 2 inches wide and ¾ to 1 inch deep.

*Stem*.—Medium thickness; about 1 inch long and ⅛ of an inch in diameter, color: Yellow Green (10 Y 7/8).

*Crowning at calyx end*.—Absent.

*Aperture of the eye*.—Closed.

*Sepals at eye basin*.—Surface texture is downy; color Gray Green (2.5 GY 7/4).

*Eye basin*.—About ½ to ¾ of an inch deep and about 1½ to 1¾ inches wide; fine pubescence observed as present; shape: slightly furrowed.

*Skin*.—Intensity of color is bright; bloom of skin is absent; greasiness is absent.

*Skin lenticels*.—Generally distinct; numbers about 15 per square inch appearing at the stem end of the fruit and about 75 per square inch appearing at the calyx end of the fruit; surface texture of lenticels is generally smooth.

*Skin lenticel color*.—Pale Pink (10 R 9/2); size of lenticels: variable from 1/64 to 1/32 of an inch.

*Core*.—Generally 1 inch in size average; core position is Basal Clasping.

*Locules*.—Shape is narrow, closed; size of locule: ⅛ of an inch by ½ of an inch. Locules number 5 per apple. There are 1-2 seeds per locule.

*Tube*.—Shape is cone shaped.

*Stamen position*.—Generally considered median.

*Axis position*.—Considered closed.

*Seed*.—Number: Generally six seeds, occasionally ten; shape: acuminate; length: 3/16 of an inch; width: about ¼ of an inch; color is Dark Brown (5 YR 2/4).

*Fruit flesh*.—Generally very firm, crisp, and juicy; color is Creamy Yellow (5 Y 9/4).

*Fruit aroma*.—Considered mild and typical for the species.

*Starch*.—Generally about 4 out of 6 starch level in iodine at prime maturity. Acids are 0.5% acidity.

*Fruit pressure*.—19.

*Soluble solids*.—14.

*Skin color*.—Generally Solid Red Blush.

*Generally red in color over* 70%-90% *of the fruit; color ranges*.—From Medium Red (5 R 4/10) to Dark Red (2.5 R 3/4).

*Ground color of the skin*.—Light Greenish Yellow (10 Y 8.5/6).

*Russetting*.—Absent.

Harvest:

*Yield*.—'Lewis' trees yield approximately 50 pounds of apples per tree in the 5$^{th}$ leaf. This yield is similar to a standard 'Honeycrisp' yield from a tree of the same age.

*Individual fruit weight*.—'Lewis' apples typically weight from 8 ounces to 14 ounces, similar to typical 'Honeycrisp' individual fruit weight.

*Tendency to crack*.—Tendency to crack is similar to standard Honeycrisp; however, because the fruit is redder, it is more likely to be picked at earlier fruit maturity, which leads to less cracking.

*Cold storage*.—Good condition when in cold storage for 200+ days at 38° F.

*Market use*.—Dessert, baking and juice.

*Harvest date*.—September 15$^{th}$ in East Wenatchee, Wash. during 2012.

COMPARISON OF HARVEST DATE

TABLE 1

Table 1: Harvest date for 'Lewis' and 'Honeycrisp' in East Wenatchee, Washington.

| Variety (*) | 2011 harvest dates | 2012 harvest dates |
|---|---|---|
| 'Honeycrisp' (U.S. Plant Pat. No. PP7,197) | September 20$^{th}$ | September 18$^{th}$ |
| 'Lewis' | September 18$^{th}$ | September 15$^{th}$ |

(*) Ready for harvest date. 'Lewis' observed in East Wenatchee, Washington; 'Honeycrisp' observed in Quincy, Washington.

I claim:

1. A new and distinct variety of apple tree, substantially as herein shown and described.

* * * * *

'Lewis' 'Honeycrisp'